United States Patent
Hu et al.

(10) Patent No.: US 12,379,342 B2
(45) Date of Patent: Aug. 5, 2025

(54) METHOD FOR DISTINGUISHING POTASSIUM CHLORATE FROM POTASSIUM BROMATE

(71) Applicant: Anhui University, Hefei (CN)

(72) Inventors: Gang Hu, Hefei (CN); Zhuo Chen, Hefei (CN); Yanke Zhou, Hefei (CN)

(73) Assignee: Anhui University, Hefei (CN)

(*) Notice: Subject to any disclaimer, the term of this patent is extended or adjusted under 35 U.S.C. 154(b) by 327 days.

(21) Appl. No.: 18/065,448

(22) Filed: Dec. 13, 2022

(65) Prior Publication Data
US 2023/0184709 A1    Jun. 15, 2023

(30) Foreign Application Priority Data
Dec. 13, 2021   (CN) .......................... 202111517707.6

(51) Int. Cl.
*G01N 27/416*   (2006.01)
*G01N 27/30*    (2006.01)
*G01N 33/18*    (2006.01)

(52) U.S. Cl.
CPC ....... *G01N 27/302* (2013.01); *G01N 27/4167* (2013.01); *G01N 33/182* (2013.01); *G01N 2223/31* (2013.01)

(58) Field of Classification Search
CPC ............. G01N 27/302; G01N 27/4146; G01N 27/4157; G01N 223/31; G01N 33/182; G01N 27/4167
See application file for complete search history.

(56) References Cited

FOREIGN PATENT DOCUMENTS

| CN | 103018184 A | * | 4/2013 | ............. G01N 21/31 |
| CN | 112051814 A | * | 12/2020 | ....... G05B 19/41875 |

OTHER PUBLICATIONS

Abu-Obaid et al., "Determination and Degradation of Potassium Bromate Content in Dough and Bread Samples Due to the Presence of Metals," American Journal of Analytical Chemistry, 2016, 7, 487-493 (Year: 2016).*
EPO machine-generated English language translation of CN 103018184 A, patent published Apr. 3, 2013 (Year: 2013).*
EPO machine-generated English language translation of CN 112051814 A, patent published Dec. 8, 2020 (Year: 2020).*
NIST potassium chlorate IR spectrum, Mar. 2017, https://webbook.nist.gov/cgi/cbook.cgi?ID=C3811049&Mask=80#IR-Spec (Year : 2017).*
NIST potassium bromate IR spectrum, 2018, https://webbook.nist.gov/cgi/inchi?ID=B6000522&Mask=80 (Year: 2018).*

* cited by examiner

*Primary Examiner* — Alexander S Noguerola
(74) *Attorney, Agent, or Firm* — Stonebridge IP, PLLC

(57) ABSTRACT

The present disclosure provides a method for distinguishing potassium chlorate from potassium bromate, including the following steps: using a "$HCHO-NaHSO_3-Na_2SO_3$" pH clock system as a distinguishing solution, and distinguishing the potassium chlorate and the potassium bromate according to different responses, namely different induction times, of the pH clock system, caused by the potassium chlorate and the potassium bromate, respectively. In the present disclosure, the pH clock system provided by the distinguishing method has an intuitive graph, and can easily and quickly distinguish the potassium chlorate and the potassium bromate; meanwhile, the distinguishing method has simple equipment, a high accuracy, and easy operation and observation.

4 Claims, 5 Drawing Sheets

METHOD FOR DISTINGUISHING POTASSIUM CHLORATE FROM POTASSIUM BROMATE

CROSS REFERENCE TO RELATED APPLICATION

This patent application claims the benefit and priority of Chinese Patent Application No. 202111517707.6, filed with the China National Intellectual Property Administration on Dec. 13, 2021, the disclosure of which is incorporated by reference herein in its entirety as part of the present application.

TECHNICAL FIELD

The present disclosure relates to a method for analyzing and distinguishing analytes, in particular to establishing a pH clock system with "HCHO—NaHSO$_3$—Na$_2$SO$_3$" as a matrix, and belongs to the field of analytical chemistry. The qualitative analysis of potassium chlorate (KClO$_3$) and potassium bromate (KBrO$_3$) is achieved according to different responses, namely different induction times, of the pH clock system to different halates.

BACKGROUND

Salts composed of halate ions and alkali metals, such as potassium chlorate (KClO$_3$) and potassium bromate (KBrO$_3$), are widely present in aqueous solutions and have different effects on human production and life. The potassium chlorate solution has low stability and strong oxidizing properties, and belongs to the controlled items that are prone to explosions, which are not allowed to contact with organic materials and reducing substances. The potassium bromate is a regulated contaminant in water and is classified as a class 2B potential carcinogen by the International Agency for Research on Cancer. In addition, since easily electrochemically reduced to their corresponding reduced forms during chemical disinfection of aqueous solutions, chlorate and bromate have received considerable attention due to their chronic toxicity. Therefore, the identification of halates is of great significance for the development of scientific research, the health of human life, and the improvement of global environment.

Since potassium chlorate and potassium bromate solutions are colorless, odorless, clear, and transparent liquids, it is difficult to distinguish the potassium chlorate from potassium bromate intuitively, bringing challenges to qualitative analysis. At present, the reported methods for distinguishing potassium chlorate from potassium bromate mainly depend on instrumental analysis, including ion chromatography (IC), mass spectrometry, and ion chromatography-mass spectrometry (IC-MS); there are also reports of optical methods for determination, such as chemiluminescence, spectrophotometry, and flow injection (FI) on-line solid phase extraction (SPE)-based fluorescence method. IC and IC-MS each have high sensitivity and desirable accuracy. However, for samples with complex matrices, the IC has reduced analytical sensitivity, while the IC-MS has higher sensitivity and accuracy but requires instruments that are still difficult to be popularized. Therefore, it is extremely necessary to find a detection and analysis method with desirable detection effect as well as simple and rapid operation.

SUMMARY

The present disclosure aims to provide a novel, convenient, and quick method for distinguishing potassium chlorate from potassium bromate, namely a method for qualitatively distinguishing the KClO$_3$ from the KBrO$_3$ using a "HCHO—NaHSO$_3$—Na$_2$SO$_3$" pH clock reaction system as a distinguishing solution. The method is developed based on a sensitive response of the pH clock system to the KClO$_3$ and the KBrO$_3$. Specifically, the method includes the following steps: using a "HCHO—NaHSO$_3$—Na$_2$SO$_3$" pH clock system as a distinguishing solution, and recording a graph of pH value changes with time; when a pH clock reaction starts, adding equal volumes of samples (the potassium chlorate and the potassium bromate) with a same concentration to two groups of the pH clock systems, respectively; and distinguishing the samples according to different induction times of the pH clock system caused by the samples: if the induction time of the pH clock is prolonged to a small extent after the sample solution is added, determining the sample as the potassium chlorate; if the induction time of the pH clock is prolonged to a large extent after the sample solution is added, determining the sample as the potassium bromate. Meanwhile, the present disclosure has a short treatment time for samples, simple and easy-to-control measurement conditions, and convenient popularization and application.

The difference between the qualitative distinguishing method and the prior art is that: in the present disclosure, a "HCHO—NaHSO$_3$—Na$_2$SO$_3$" pH clock system is used as a distinguishing solution, and the potassium chlorate is qualitatively distinguished from the potassium bromate according to different responses, namely different induction times of the pH clock system, caused by the potassium chlorate and the potassium bromate, respectively.

The potassium chlorate and the potassium bromate have a distinguishable concentration range of $5.0 \times 10^{-4}$ mol/L to $2.5 \times 10^{-3}$ mol/L in the distinguishing solution (pH clock system).

The pH clock system is controlled at any specific temperature in a range of 20° C. to 25° C. when distinguishing the sample solution.

The distinguishable concentration range of the sample solution is an optimal concentration range determined by experiments. Within this concentration range, the influences of potassium chlorate and potassium bromate on the distinguishing solution have an extremely obvious difference, which is easy to observe and analyze to achieve distinguishing easily. In addition, a concentration range of each component in the distinguishing solution (pH clock system) is shown in Table 1; and an optimal concentration of the distinguishing solution (pH clock system) obtained after many experiments is shown in Table 2:

TABLE 1

| Concentration of each component in pH clock system | | |
|---|---|---|
| HCHO (mol/L) | NaHSO$_3$ (mol/L) | Na$_2$SO$_3$ (mol/L) |
| 0.045-0.0625 | 0.045-0.0625 | 0.0045-0.00625 |

TABLE 2

| Optimal concentration of each component in pH clock system | | |
|---|---|---|
| HCHO(mol/L) | NaHSO$_3$(mol/L) | Na$_2$SO$_3$(mol/L) |
| 0.051 | 0.0495 | 0.00495 |

The specific experimental steps were as follows:

1. A distinguishing solution (pH clock system) is prepared according to the concentration range specified in Table 1, and its temperature is controlled at a specific value of 20° C. to 25° C. and remains unchanged; one end of a prepared working electrode (pH composite electrode, Lei-Ci, E-331) is inserted into the distinguishing solution, and the other end of the working electrode is connected to a computer through a potential/temperature/pH comprehensive tester (JiaxingDisheng Electronic Technology Co., Ltd., ZHFX-595, Zhejiang, China); after running a Chemical Signal Acquisition and Analysis program in the computer to set the acquisition time and sampling speed, the START button is quickly pressed to monitor a pH value of the sample solution. The computer records a curve of the collected pH value with time, that is, the pH clock graph (the samples have not been added at this time), which is used as a blank control. When the reaction of the pH clock system starts, the sample solutions are rapidly added to the distinguishing solutions with the same concentration of each component in the two groups, and the pH clock graph of pH value changes with time is recorded in the same way; according to the different responses, namely the different induction times of the pH clock system caused by the samples, the qualitative analysis of the samples is realized. Specifically: if the induction time of the pH clock is prolonged to a small extent after the sample solution is added, determining the sample as the potassium chlorate; if the induction time of the pH clock is prolonged to a large extent after the sample solution is added, determining the sample as the potassium bromate.

The basic parameters of the pH clock graph include:

induction time: the duration from the start of the pH clock system reaction to the pH jump; and pH jump range: a pH value corresponding to the start of the pH jump to a pH value corresponding to the end of the pH jump.

DETAILED DESCRIPTION OF THE EMBODIMENTS

Example 1

In this example, feasibility of a method for distinguishing potassium chlorate from potassium bromate of the present disclosure was verified as follows:

(1) Preparation of Sample Solutions

A mixed solution of 0.2 mol/L HCHO, 0.1 mol/L $NaHSO_3$, and 0.01 mol/L $Na_2SO_3$ was prepared with distilled water. 10.0 mL of a distilled water solution, 19.8 mL of a $NaHSO_3$—$Na_2SO_3$ mixed solution, and 10.2 mL of a 0.2 mol/L HCHO solution were added to a 50 mL small beaker in sequence, to ensure that a "HCHO—$NaHSO_3$—$Na_2SO_3$" pH clock system had 0.051 mol/L of HCHO, 0.0495 mol/L of $NaHSO_3$, and 0.00495 mol/L of $Na_2SO_3$, and had a total volume of 40 mL and a temperature controlled at 25° C.

0.1 mol/L of a potassium chlorate solution and 0.1 mol/L of a potassium bromate solution were prepared with distilled water as a solvent.

(2) Obtaining a pH Clock Graph

Figure 1:
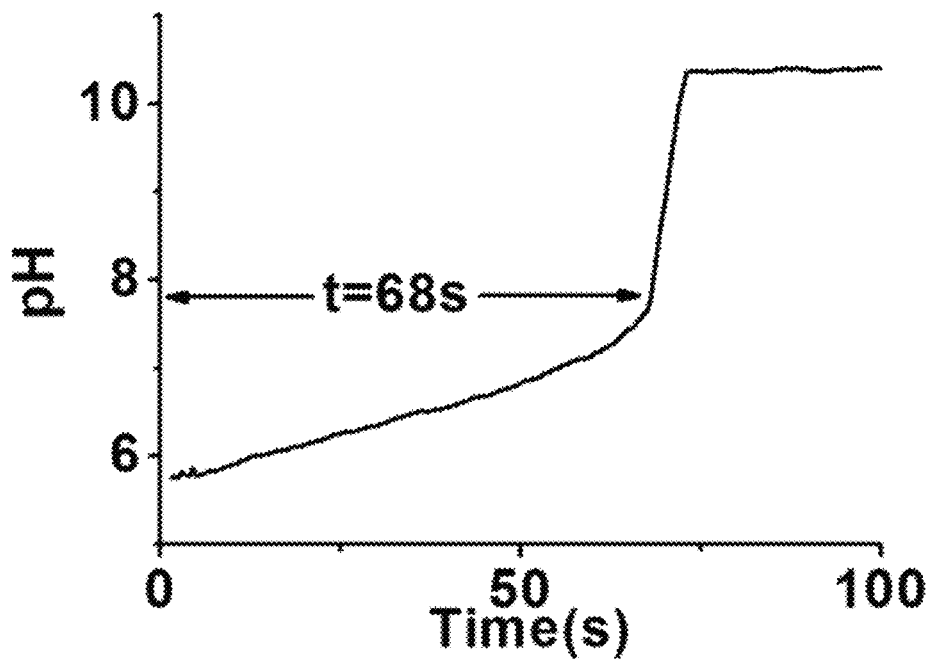
FIG. 1 shows a graph of changes of a pH value with time of a distinguishing solution (pH clock system) when a sample to be distinguished is not added in Example 1.
Figure 2:
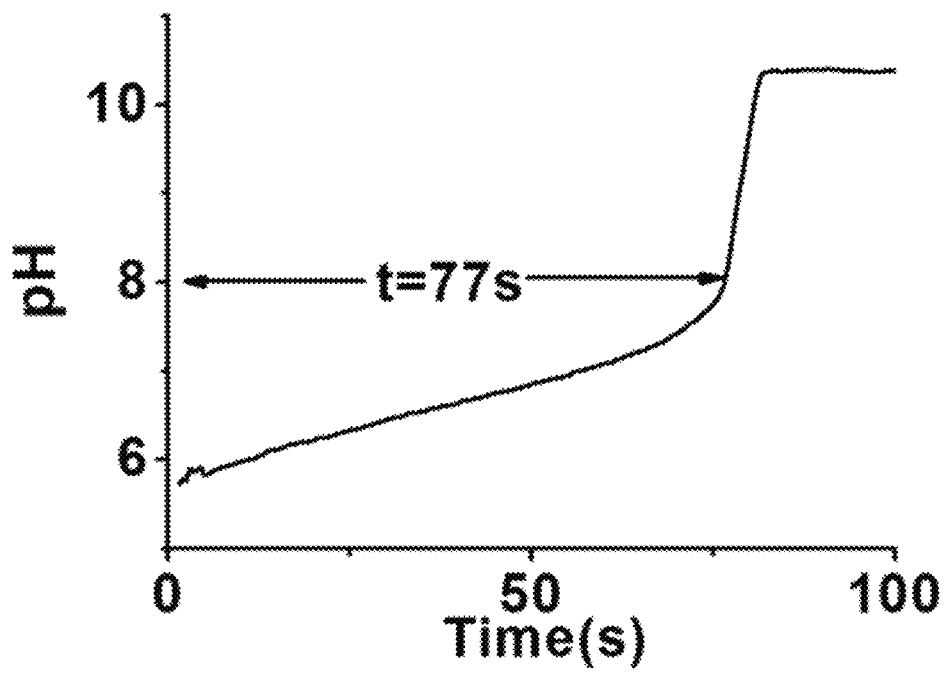
FIG. 2 shows a graph of changes of a pH value with time of the distinguishing solution (pH clock system) when $5\times10^4$ mol/L $KClO_3$ is added in Example 1.
Figure 3:
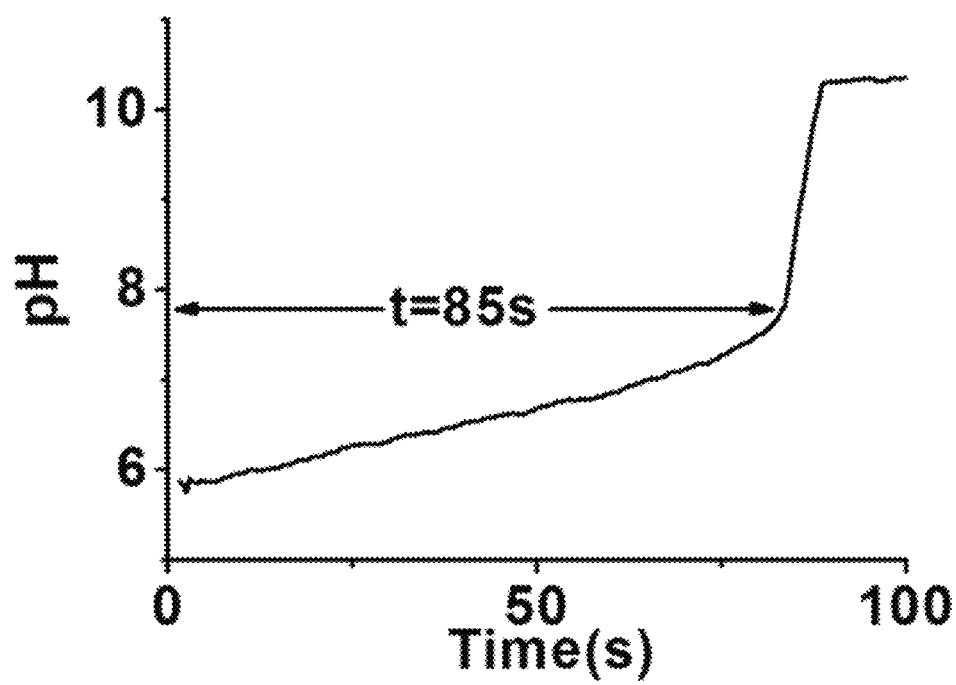
FIG. 3 shows a graph of changes of a pH value with time of the distinguishing solution (pH clock system) when $5\times10^4$ mol/L $KBrO_3$ is added in Example 1.

A graph of pH value changes of the distinguishing solution over time was recorded by a computer equipped with a Chemical Signal Acquisition and Analysis program (no sample was added), as shown in FIG. 1. A pH induction time at 68 sec was used as a blank control. Another two groups of distinguishing solutions were prepared with the same concentration of each component as those in the above distinguishing solutions. For one group, 200 μL of a 0.1 mol/L potassium chlorate sample solution was added to 40 mL of the pH clock system at the same time as the reaction started, such that the concentration of potassium chlorate in the distinguishing solution was $5\times10^4$ mol/L, the added potassium chlorate prolonged the induction time to 77 sec, as shown in FIG. 2. For the other group, 200 μL of a 0.1 mol/L potassium bromate sample solution was added to 40 mL of the pH clock system at the same time as the reaction started, such that the concentration of potassium bromate in the distinguishing solution was $5\times10^4$ mol/L, the added potassium bromate prolonged the induction time to 85 sec, as shown in FIG. 3.

(3) Distinguishing

Potassium chlorate and potassium bromate have different influences on the induction time of the pH clock system due to their different chemical property. Comparing FIG. 2 and FIG. 3, it was seen that the potassium chlorate prolonged the induction time of the pH clock to a small extent; while the potassium bromate resulted in a considerable prolongation of the induction time of the pH clock. It was seen from the above experiments that the potassium chlorate can be distinguished from the potassium bromate by comparing the changes in the induction time of the pH clock system.

Two pre-prepared 0.1 mol/L solutions of the sample were taken (one was a potassium chlorate solution and the other was a potassium bromate solution, which were not distinguished), and one of them was marked as a sample 1 and the other was marked as a sample 2; and two groups of pH clock system solutions with the same concentration of each component as above were prepared; 200 μL of the sample 1 at 0.1 mol/L and 200 μL of the sample 2 at 0.1 mol/L were added at the start of the pH clock, such that concentrations of the two samples in the distinguishing solution each were $5\times10^4$ mol/L, and corresponding perturbed graph of a pH value with time were collected, respectively.

Analysis and comparison showed that: the sample 1 prolonged the induction time of the pH clock to a small extent (a pattern corresponded to FIG. 2, but did not correspond to FIG. 3); while the sample 2 prolonged the induction time of the pH clock to a large extent (a pattern corresponded to FIG. 3, but did not correspond to FIG. 2). Therefore, the sample 1 was a potassium chlorate solution, and the sample 2 was a potassium bromate solution, thereby distinguishing the potassium chlorate solution from the potassium bromate solution.

Example 2

In this example, feasibility of a method for distinguishing potassium chlorate from potassium bromate of the present disclosure was verified as follows:
(1) Preparation of Sample Solutions
A mixed solution of 0.2 mol/L HCHO, 0.1 mol/L $NaHSO_3$, and 0.01 mol/L $Na_2SO_3$ was prepared with distilled water. 9.5 mL of a distilled water solution, 20.0 mL of a $NaHSO_3$—$Na_2SO_3$ mixed solution, and 10.5 mL of a 0.2 mol/L HCHO solution were added to a 50 mL small beaker in sequence, to ensure that a "HCHO—$NaHSO_3$—$Na_2SO_3$" pH clock system had 0.0525 mol/L of HCHO, 0.05 mol/L of $NaHSO_3$, and 0.005 mol/L of $Na_2SO_3$, and had a total volume of 40 mL and a temperature controlled at 25° C.

0.1 mol/L of a potassium chlorate solution and 0.1 mol/L of a potassium bromate solution were prepared with distilled water as a solvent.

Figure 4:
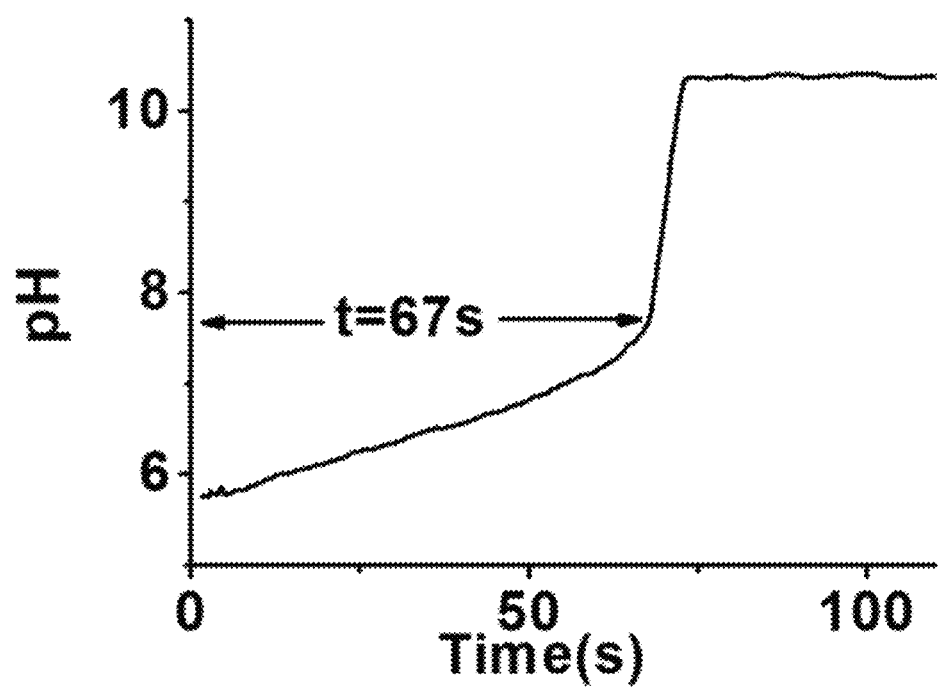
FIG. 4 shows a graph of changes of a pH value with time of the distinguishing solution (pH clock system) when the sample to be distinguished is not added in Example 2.
Figure 5:
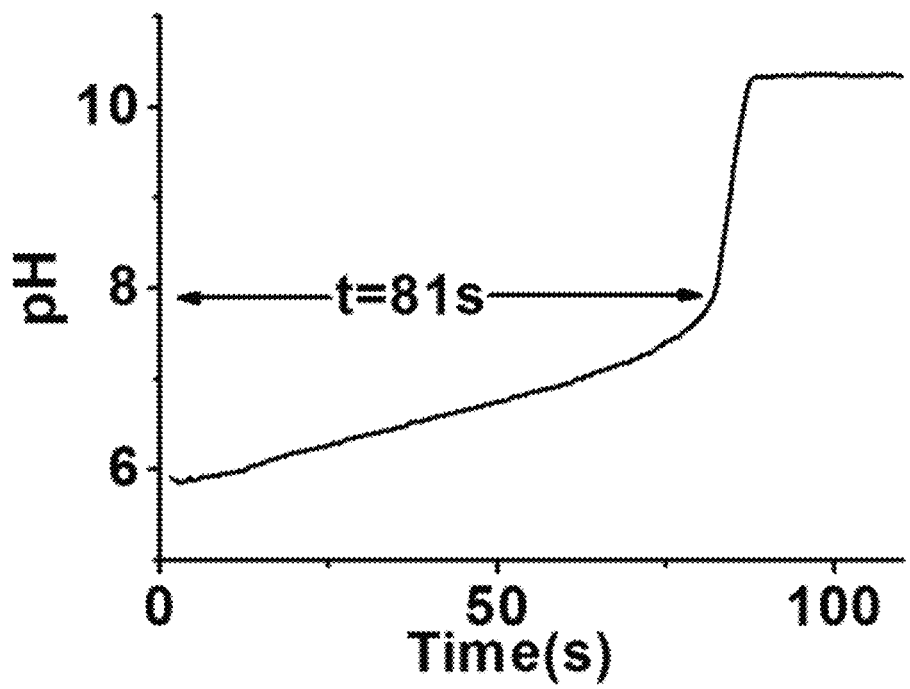
FIG. 5 shows a graph of changes of a pH value with time of the distinguishing solution (pH clock system) when $1\times10^{-3}$ mol/L $KClO_3$ is added in Example 2.

(2) Obtaining a pH Clock Graph
A graph of pH value changes of the distinguishing solution over time was recorded by a computer equipped with a Chemical Signal Acquisition and Analysis program (no sample was added), as shown in FIG. 4. A pH induction time at 67 sec was used as a blank control. Another two groups of distinguishing solutions were prepared with the same concentration of each component as those in the above distinguishing solutions. For one group, 400 μL of a 0.1 mol/L potassium chlorate sample solution was added to 40 mL of the pH clock system at the same time as the reaction started, such that the concentration of potassium chlorate in the distinguishing solution was $1.0 \times 10^{-3}$ mol/L, the added potassium chlorate prolonged the induction time to 81 sec, as shown in FIG. 5. For the other group, 400 μL of a 0.1 mol/L potassium bromate sample solution was added to 40 mL of the pH clock system at the same time as the reaction started, such that the concentration of potassium bromate in the distinguishing solution was $1.0 \times 10^{-3}$ mol/L, the added potassium bromate prolonged the induction time to 88 sec, as shown in FIG. 6.

(3) Distinguishing
Potassium chlorate and potassium bromate have different influences on the induction time of the pH clock system due to their different chemical property. Comparing FIG. 5 and FIG. 6, it was seen that the potassium chlorate prolonged the induction time of the pH clock to a small extent; while the potassium bromate resulted in a considerable prolongation of the induction time of the pH clock. It was seen from the above experiments that the potassium chlorate can be distinguished from the potassium bromate by comparing the changes in the induction time of the pH clock system.

Two pre-prepared 0.1 mol/L solutions of the sample were taken (one was a potassium chlorate solution and the other was a potassium bromate solution, which were not distinguished), and one of them was marked as a sample 1 and the other was marked as a sample 2; and two groups of pH clock system solutions with the same concentration of each component as above were prepared; 400 μL of the sample 1 at 0.1 mol/L and 400 μL of the sample 2 at 0.1 mol/L were added at the start of the pH clock, such that concentrations of the two samples in the distinguishing solution each were $1 \times 10^{-3}$ mol/L, and corresponding perturbed graph of a pH value with time were collected, respectively.

Figure 6:
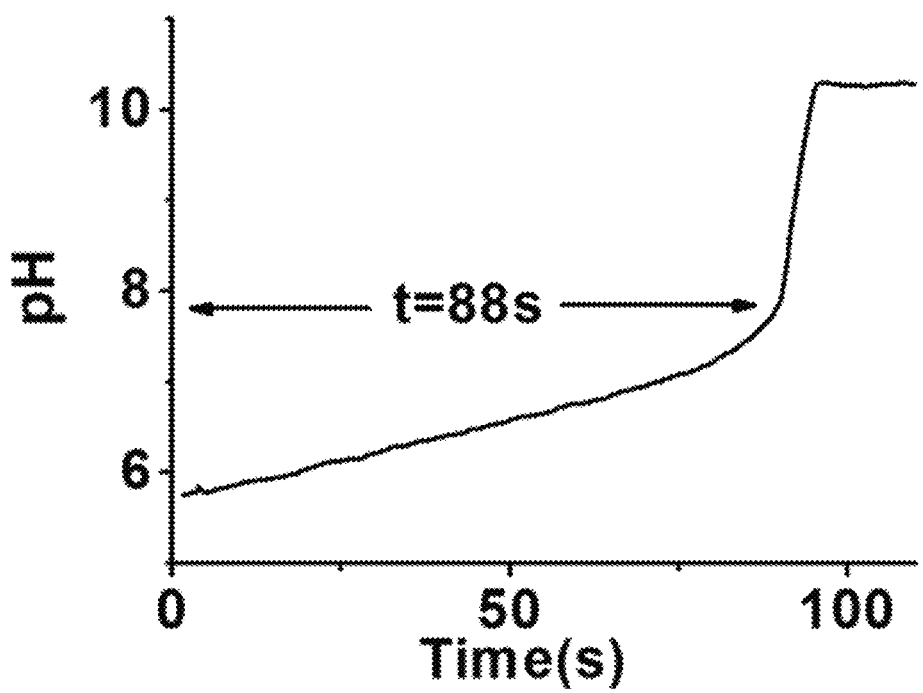
FIG. 6 shows a graph of changes of a pH value with time of the distinguishing solution (pH clock system) when $1\times10^{-3}$ mol/L $KBrO_3$ is added in Example 2.

Analysis and comparison showed that: the sample 1 prolonged the induction time of the pH clock to a small extent (a pattern corresponded to FIG. 5, but did not correspond to FIG. 6); while the sample 2 prolonged the induction time of the pH clock to a large extent (a pattern corresponded to FIG. 6, but did not correspond to FIG. 5). Therefore, the sample 1 was a potassium chlorate solution, and the sample 2 was a potassium bromate solution, thereby distinguishing the potassium chlorate solution from the potassium bromate solution.

Example 3

In this example, feasibility of a method for distinguishing potassium chlorate from potassium bromate of the present disclosure was verified as follows:
(1) Preparation of Sample Solutions
A mixed solution of 0.2 mol/L HCHO, 0.1 mol/L $NaHSO_3$, and 0.01 mol/L $Na_2SO_3$ was prepared with distilled water. 10.2 mL of a distilled water solution, 20 mL of a $NaHSO_3$—$Na_2SO_3$ mixed solution, and 9.8 mL of a 0.2 mol/L HCHO solution were added to a 50 mL small beaker in sequence, to ensure that a "HCHO—$NaHSO_3$—$Na_2SO_3$" pH clock system had 0.049 mol/L of HCHO, 0.05 mol/L of $NaHSO_3$, and 0.005 mol/L of $Na_2SO_3$, and had a total volume of 40 mL and a temperature controlled at 25° C.

0.1 mol/L of a potassium chlorate solution and 0.1 mol/L of a potassium bromate solution were prepared with distilled water as a solvent.

Figure 7:
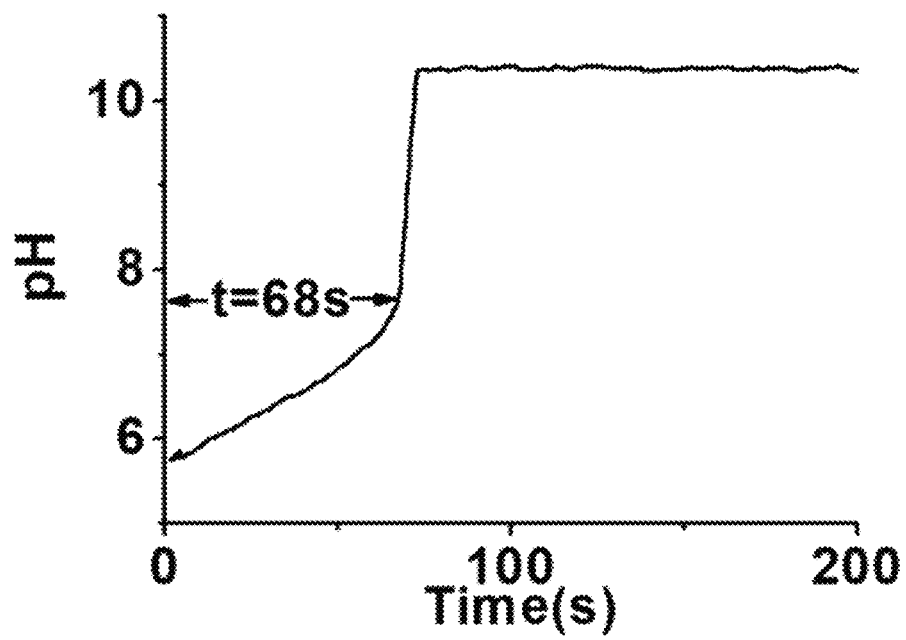
FIG. 7 shows a graph of changes of a pH value with time of the distinguishing solution (pH clock system) when the sample to be distinguished is not added in Example 3.
Figure 8:
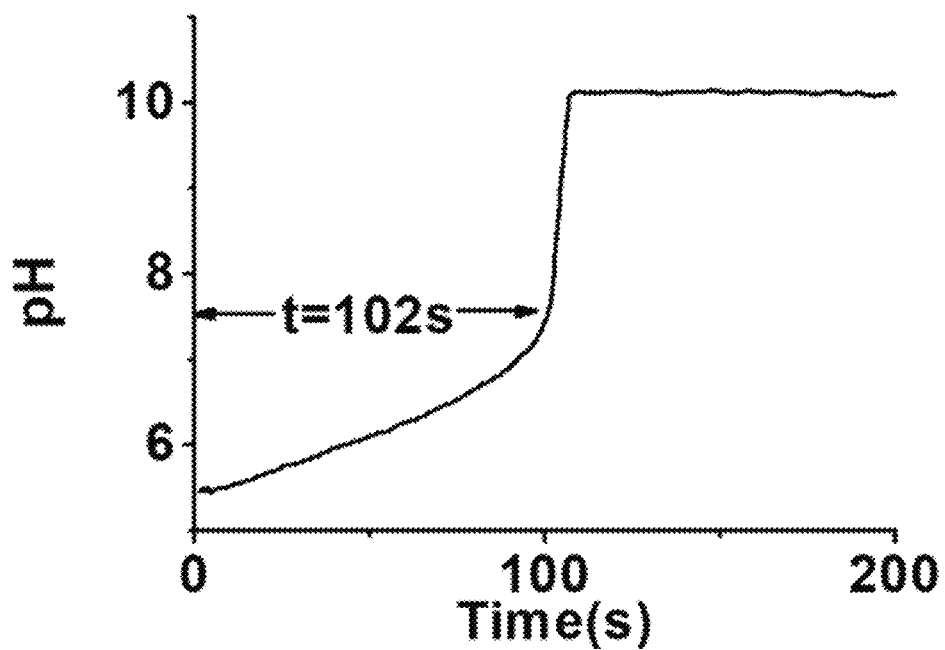
FIG. 8 shows a graph of changes of a pH value with time of the distinguishing solution (pH clock system) when $2\times10^{-3}$ mol/L $KClO_3$ is added in Example 3.

(2) Obtaining a pH Clock Graph
A graph of pH value changes of the distinguishing solution over time was recorded by a computer equipped with a Chemical Signal Acquisition and Analysis program (no sample was added), as shown in FIG. 7. A pH induction time at 68 sec was used as a blank control. Another two groups of distinguishing solutions were prepared with the same concentration of each component as those in the above distinguishing solutions. For one group, 800 μL of a 0.1 mol/L potassium chlorate sample solution was added to 40 mL of the pH clock system at the same time as the reaction started, such that the concentration of potassium chlorate in the distinguishing solution was $2.0 \times 10^{-3}$ mol/L, the added potassium chlorate prolonged the induction time to 102 sec, as shown in FIG. 8. For the other group, 800 μL of a 0.1 mol/L potassium bromate sample solution was added to 40 mL of the pH clock system at the same time as the reaction started, such that the concentration of potassium bromate in the distinguishing solution was $2.0 \times 10^{-3}$ mol/L, the added potassium bromate prolonged the induction time to 123 sec, as shown in FIG. 9.

(3) Distinguishing
Potassium chlorate and potassium bromate have different influences on the induction time of the pH clock system due to their different chemical property. Comparing FIG. 8 and FIG. 9, it was seen that the potassium chlorate prolonged the induction time of the pH clock to a small extent; while the potassium bromate resulted in a considerable prolongation of the induction time of the pH clock. It was seen from the above experiments that the potassium chlorate can be distinguished from the potassium bromate by comparing the changes in the induction time of the pH clock system.

Two pre-prepared 0.1 mol/L solutions of the sample were taken (one was a potassium chlorate solution and the other was a potassium bromate solution, which were not distinguished), and one of them was marked as a sample 1 and the other was marked as a sample 2; and two groups of pH clock system solutions with the same concentration of each component as above were prepared; 800 μL of the sample 1 at 0.1 mol/L and 800 μL of the sample 2 at 0.1 mol/L were added at the start of the pH clock, such that concentrations of the two samples in the distinguishing solution each were $2 \times 10^{-3}$ mol/L, and corresponding perturbed graph of a pH value with time were collected, respectively.

Figure 9:
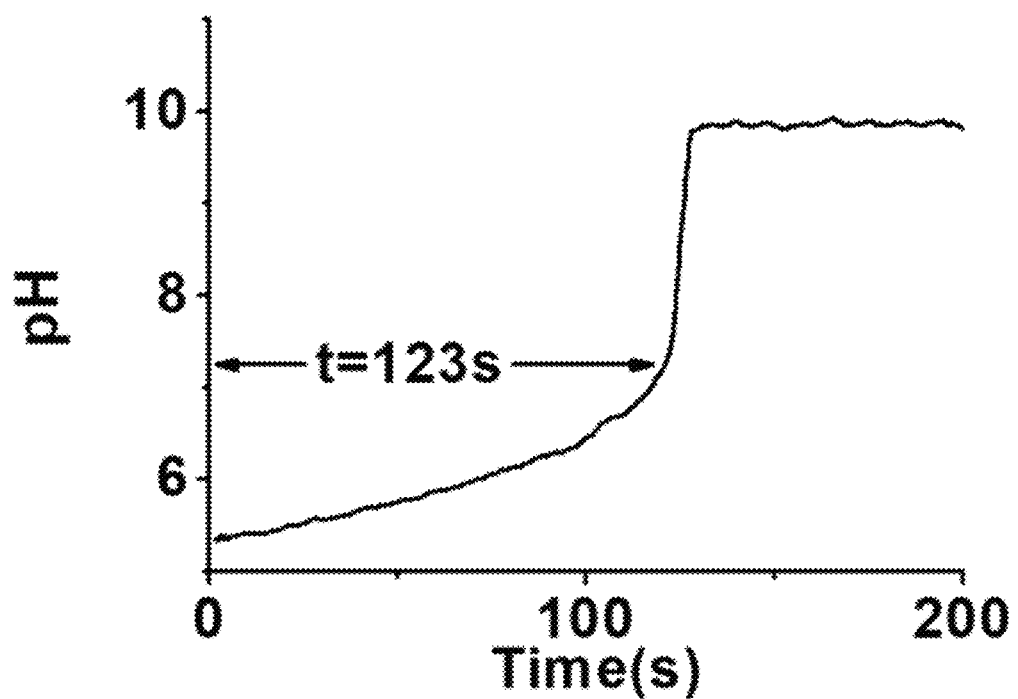
FIG. 9 shows a graph of changes of a pH value with time of the distinguishing solution (pH clock system) when $2\times10^{-3}$ mol/L $KBrO_3$ is added in Example 3.

Analysis and comparison showed that: the sample 1 prolonged the induction time of the pH clock to a small extent (a pattern corresponded to FIG. 8, but did not correspond to FIG. 9); while the sample 2 prolonged the induction time of the pH clock to a large extent (a pattern corresponded to FIG. 9, but did not correspond to FIG. 8). Therefore, the sample 1 was a potassium chlorate solution, and the sample 2 was a potassium bromate solution, thereby distinguishing the potassium chlorate solution from the potassium bromate solution.

It can be seen from the above examples that the potassium chlorate solution and the potassium bromate solution with a smaller or greater concentration can also be distinguished by the method of the present disclosure.

What is claimed is:

1. A method for distinguishing potassium chlorate from potassium bromate, comprising the following steps:
   providing two same distinguishing solutions, which are controlled at a temperature in a range of 20° C. to 25° C.;
   simultaneously adding two sample solutions of an equal volume with a same concentration separately into the two same distinguishing solutions, and recording graphs of pH value changes of two resulting solutions over time, wherein the two sample solutions are a potassium chlorate solution and a potassium bromate solution, both with distilled water as a solvent; and
   distinguishing the potassium chlorate sample solution from the potassium bromate sample solution according to different induction times of the two resulting solutions: wherein a small extension of the induction time for a resulting solution indicates that sample solution being added is the potassium chlorate solution; and a large extension of the induction time for a resulting solution indicates that sample solution being added is the potassium bromate solution; wherein
   the two same distinguishing solutions have 0.045 mol/L to 0.0625 mol/L of HCHO, 0.045 mol/L to 0.0625 mol/L of $NaHSO_3$, and 0.0045 mol/L to 0.00625 mol/L of $Na_2SO_3$; and
   a sample concentration in each of the two resulting solutions is in a range of $5.0 \times 10^{-4}$ mol/L to $2.0 \times 10^{-3}$ mol/L.

2. The method according to claim 1, wherein the two same distinguishing solutions haves 0.051 mol/L of the HCHO, 0.0495 mol/L of the $NaHSO_3$, and 0.00495 mol/L of the $Na_2SO_3$.

3. The method according to claim 1, wherein the two same distinguishing solutions are controlled at 25° C. during adding and recording steps.

4. A method for distinguishing potassium chlorate from potassium bromate, comprising the following steps:
   providing two same distinguishing solutions, which are controlled at a temperature in a range of 20° C. to 25° C.;
   simultaneously adding two sample solutions of an equal volume with a same concentration separately into the two same distinguishing solutions, and recording graphs of pH value changes of two resulting solutions over time, wherein the two sample solutions are a potassium chlorate solution and a potassium bromate solution, both with distilled water as a solvent; and
   distinguishing the potassium chlorate sample solution from the potassium bromate sample solution by comparing induction times of the two resulting solutions, wherein a shorter induction time of a resulting solution indicates that sample solution being added is the potassium chlorate solution; and a longer induction time of a resulting solution indicates that sample solution being added is the potassium bromate solution; wherein
   the two same distinguishing solutions have 0.045 mol/L to 0.0625 mol/L of HCHO, 0.045 mol/L to 0.0625 mol/L of $NaHSO_3$, and 0.0045 mol/L to 0.00625 mol/L of $Na_2SO_3$; and
   a sample concentration in each of the two resulting solutions is in a range of $5.0 \times 10^{-4}$ mol/L to $2.0 \times 10^{-3}$ mol/L.

* * * * *